United States Patent [19]

Buendia et al.

[11] Patent Number: 5,731,447
[45] Date of Patent: Mar. 24, 1998

[54] PROCESS FOR PREPARING 16α-METHYL-STEROIDS

[75] Inventors: Jean Buendia, Le Perreux Sur Marne; Patrick Roussel, Thiais; Michel Vivat, Lagny Sur Marne, all of France

[73] Assignee: Roussel Uclaf, France

[21] Appl. No.: 660,817

[22] Filed: Jun. 10, 1996

Related U.S. Application Data

[63] Continuation of Ser. No. 452,088, May 26, 1995, abandoned, which is a continuation of Ser. No. 73,760, Jun. 8, 1993, abandoned.

[30] Foreign Application Priority Data

Jun. 11, 1992 [FR] France .................... 92 07048

[51] Int. Cl.⁶ .................................... C07J 5/00
[52] U.S. Cl. .................. 552/574; 552/593; 540/89; 540/87; 540/20; 540/16; 540/22
[58] Field of Search .................... 552/574, 593; 540/89

[56] References Cited

U.S. PATENT DOCUMENTS 4,530,795  7/1985  Huber .

*Primary Examiner*—Rebecca Cook
*Attorney, Agent, or Firm*—Bierman, Muserlian and Lucas

[57] ABSTRACT

A process for the preparation of a compound of the formula

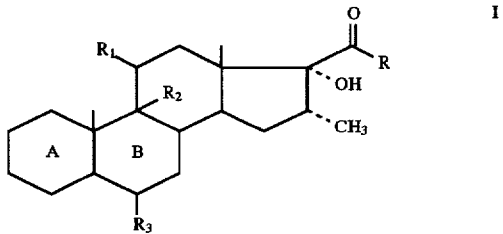

9 Claims, No Drawings

PROCESS FOR PREPARING 16α-METHYL-STEROIDS

PRIOR APPLICATION

This application is a continuation of U.S. patent application Ser. No. 452,088 filed May 26, 1995 which is a continuation of U.S. patent application Ser. No. 073,760 filed Jun. 8, 1993, both now abandoned.

STATE OF THE ART

Related prior art includes German patent No. 2,407,967, British patent application No. 2,001,990, PCT application WO 87-07612 and U.S. Pat. No. 4,530,795.

OBJECTS OF THE INVENTION

It is an object of the invention to provide an improved process for the preparation of 16α-methyl-steroids and novel intermediates produced therein.

THE INVENTION

The novel process of the invention a process for the preparation of a compound of the formula

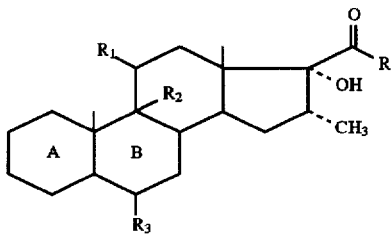

wherein the A and B rings represent a group

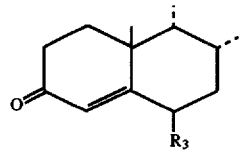

wherein the ketone function in position 3 is optionally protected in the form of a ketal, thioketal, hemithioketal or enol ether, or

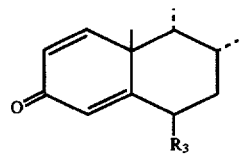

wherein R is methyl or —CH$_2$—OR', R' is hydrogen or forms an ether or ester, R$_1$ and R$_2$ form together a second bond, or R$_1$ and R$_2$ form together a β-epoxide, or R$_1$ is hydrogen, ketone or hydroxy in α- or β-position, free or protected in the form of an ether or ester and R$_2$ is hydrogen, or R$_1$ is hydrogen and R$_2$ is α-hydroxy, or R$_1$ is β-hydroxy, free or protected in the form of an ether or ester and R$_2$ is α-fluorine or bromine, and R$_3$ is hydrogen or fluorine or α- or β-methyl comprises reacting a compound of the formula

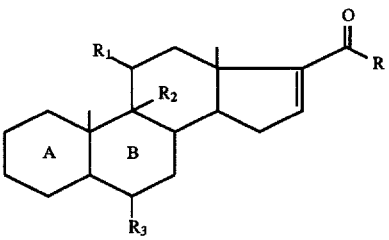

wherein A, B, R, R$_1$, R$_2$ and R$_3$ have the above meaning with a methylation agent in the presence of a copper-based catalyst, then hydrolyzing the methylated intermediate to obtain the corresponding enol and oxidizing the latter with molecular oxygen in the presence of a reducing and complexing agent of copper to obtain the compound of formula I.

When the 3-ketone function is protected in the form of a ketal, thioketal or hemithioketal, it is preferably a group of the formula:

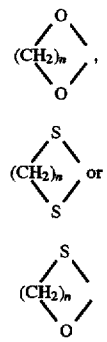

wherein n is 2 or 3 and particularly an ethylenedioxy or ethylenedithio. When the 3-ketone function is protected in the form of an enol ether, it is preferably an alkoxy or alkoxyalkoxy of 1 to 8 carbons and more particularly methoxy, ethoxy, ethoxyethoxy or 1-ethoxyethoxy, rings A and B in that case comprising a system of Δ3,5 double bonds.

When R' is an ether remainder, it can be any remainder known to one skilled in the art and preferably alkyl of 1 to 6 carbon atoms, for example methyl, ethyl or propyl, tetrahydropyranyl, or a remainder of silylated ether, for example trialkylsilyl such as trimethyl- or dimethylterbutylsilyl, triarylsilyl such as triphenylsilyl or diarylalkylsilyl such as diphenylterbutylsilyl.

When R' is an ester remainder, it can be any remainder known to one skilled in the art and preferably an acyl of 1 to 8 carbon atoms, for example formyl, acetyl, propionyl, butyryl, valeryl or benzoyl. When R$_1$ is a protected hydroxy function in the form of an ether or ester, it is an ether or ester remainder mentioned above for R', it being understood that these remainders are not necessarily identical.

In a preferred process of the invention, a compound of formula II is used in which the A and B rings are

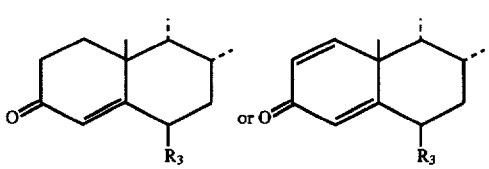

in which R$_3$ is defined as above and the 3-ketone is free. In another preferred process of the invention, a compound of formula II is used in which $R_1$ and $R_2$ form a second bond, or $R_1$ and $R_2$ form together a β-epoxide, or $R_1$ is β-hydroxy, free or protected in the form of an ether or ester and $R_2$ is α-fluorine, and $R_3$ is hydrogen, fluorine or methyl and, preferably, hydrogen.

The methylation agent can be a methylated copper derivative, for example $CH_3Cu$, $(CH_3)_2 CuMg$, $(CH_3)_2 CuLi$ or, preferably, it can be methyl-magnesium chloride, bromide or iodide, used in the presence of a copper-based catalyst. The catalyst can be a salt such as cupric acetate, propionate or chloride, cuprous chloride, bromide, iodide or cyanide, or also a complex, for example copper acetylacetonate, cuprous dimethylsulfide bromide or also cuprous tri-nbutylphosphine chloride or any other complex of the same type known to one skilled in the art. Cupric acetate and propionate are particularly preferred.

The operation takes place in a solvent which is preferably an ether such as tetrahydrofuran, dioxane, terbutylmethylether or dimethoxyethane and tetrahydrofuran is particularly preferred. The operation advantageously takes place at temperature of 0° to –30° C. and, preferably at –20° C.

The hydrolysis of the methylated intermediate is preferably carried out by pouring the reaction solution into an aqueous solution of monoalkali metal phosphate, for example sodium or potassium, or in a buffer of weakly acidic pH, notably phosphate buffer, in an aqueous solution .of ammonium chloride or, more generally, in weak acidic agent such as acetic acid, propionic acid or butyric acid.

The oxidation of the enol is carried out by bubbling oxygen through or, preferably, by bubbling air through the hydrolysis medium and the reaction takes place in the presence of a reducing and complexing agent of copper and compatible with the oxidizing agent, which is preferably dialkylsulfide, tetrahydrothiophene, trialkyl or triphenylphosphite or triphenylphosphine. Dimethyl sulfide and tetrahydrothiophene are particularly preferred and the reaction preferably takes place at ambient temperature.

The preparation of the compounds of formula I has already been described, for example in Application WO 87/07612. The process of the invention consists of methylating an unsaturated 16 derivative with a methylation agent in the presence of a copper-based catalyst and a silylation agent with the purpose of intermediately isolating a derivative of the type:

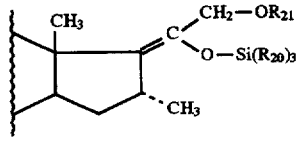

which is then treated with peracid to form the 17α-20 epoxide which is finally hydrolyzed with an acid or base.

The process of the invention does not require the isolation of any intermediate, the product resulting from the methylation reaction being directly hydrolyzed, then oxidized under conditions which have never been envisaged to date and is particularly useful from an industrial point of view. Its implementation is far more straightforward than that of known processes and particularly than that of the above Application.

British Patent No. 2,001,990 also describes a process for the preparation of compounds of formula I which consists of methylating an unsaturated 16 derivative, then preparing and isolating the hydroperoxide of the formula:

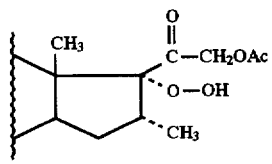

which is then reduced with zinc in acetic acid or with an alkali metal iodide in an aliphatic ketone. It should be noted 1) that such process which first isolates a hydroperoxide and then treats it with a reducing agent is not industrially viable due to the dangers inherent in these operations; and 2) that contrary to the process of the invention which permits the oxidation and the reduction to take place in a single stage by using a compatible reducing agent, the above process does not allow this due to incompatibility between the reagents used. In others words, the principle on which the process of the invention is based is different and this essentially relates to the reducing (or oxidizable) ligand that it uses and whose presence is indispensable.

The novel intermediates of the invention are compounds of the formula

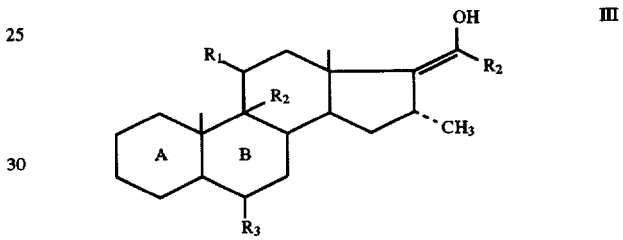

in which A, B, R, $R_1$, $R_2$ and $R_3$ have the above meanings and especially the compounds of formula III as defined above wherein the A and B rings are

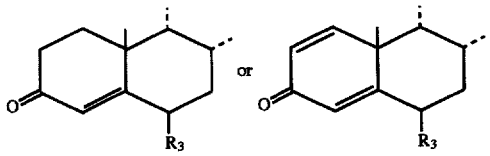

in which $R_3$ is defined as above and the 3-ketone is free and those wherein $R_1$ and $R_2$ form together a second bond, or $R_1$ and $R_2$ form together a β-epoxide or $R_1$ is β-hydroxyl free or protected as an ether form and $R_2$ is α-fluorine and $R_3$ is hydrogen, fluorine or methyl.

The compounds of formula II are known and described, for example, in U.S. Pat. Nos. 2,345,711, No. 2,883,400, No. 2,963,496, NO. 2,966,504, No. 2,975,197, No. 3,029,233, No. 3,210,341, No. 3,377,343, No. 3,839,369, No. 3,976, 638, No. 4,031,080, No. 4,277,409, No. 4,929,395, German Patent No. 2,207,420, Dutch Patent No. 69 02 507 or Belgian Patents No. 539,498, No. 540,478, No. 711,016, or can be easily prepared starting from compounds described in these Patents by processes known to one skilled in the art.

The 16α-methyl compounds of formula I are known to possess an anti-inflammatory activity and includes dexamethasone, its derivatives (6α-fluoro)-flumethasone, (6α-fluoro 9H)-paramethasone and possible precursors (Δ9, 11,9α-OH or 9,11-epoxy).

In the following examples, there are described several preferred embodiments to illustrate the invention. However, it should be understood that the invention is not intended to be limited to the specific embodiments.

EXAMPLE 1

9β, 11β-epoxy 16α-methyl-21-acetyloxy-Δ1,4-pregnadiene-17α-ol-3,20-dione 0.1 g of monohydric cupric acetate, 3.83 g of 9β,11β-epoxy 21-acetyloxy-Δ1,4,16(17)-pregnatriene 3,20-dione and 50 ml of tetrahydrofuran were mixed together at 20° C. under an inert gas atmosphere for 15 minutes and then the solution was cooled to –20° C. 3.75 ml of 3M solution of methyl magnesium bromide in ethyl ether were slowly introduced and the mixture was stirred for one hour at –20° C. 40 ml of 13.6% aqueous solution of monopotassium phosphate cooled to approximately 0° C. was admixed with the above mixture with stirring over about 5 minutes. The temperature of the enol solution was allowed to rise with stirring and then 4 ml of dimethylsulfide were added at +15° C. in the presence of air. Air was bubbled through the mixture with stirring while allowing the temperature to rise and condensing the entrained dimethylsulfide. After 3 hours, another 2 ml of dimethylsulfide were added and the bubbling through of air was continued for 2 hours. After decanting and extracting with ethyl acetate, the organic phase was washed with water, dried and the solvent was evaporated. The residue was chromatographed on silica eluting with methylene chloride - ether mixture (7-3) to obtain 3.124 g of the expected crystallized product.

IR Spectrum ($CHCl_3$)

Absorptions at 3616 $cm^{-1}$ (OH), 1747-1728 $cm^{-1}$ (C=O), 1663-1624-1607 $cm^{-1}$ (Δ1,4 3-one).

NMR Spectrum ($CDCl_3$, 300 MHz, ppm)

0.88: 16-$CH_3$; 0.93: H of 18-$CH_3$; 1.44: H of 19-$CH_3$; 2.16: $CH_3$ of OAc; 2.94: H of 17-OH; 3.21: H in position 11; 4.69–5.04: 2H in position 21; 6.14: H in position 4; 6.20: H in position 2; 6.62: H in position 1.

Analysis of the intermediate enol:

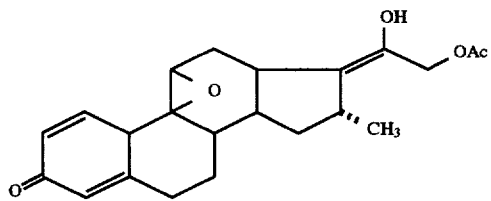

IR Spectrum ($CHCl_3$) (under inert atmosphere)

3588+associated 3430 $cm^{-1}$ (F): OH; 1738 $cm^{-1}$ (shoulder), 1718 $cm^{-1}$ (max): >=O; 1663 $cm^{-1}$ >=O, 1625 $cm^{-1}$ C=C, 1607 $cm^{-1}$ conjugated:$Δ_{1-4}$ 3-one.

RMN Spectrum ($CDCl_3$, 400 MHz, ppm)

5.17 and 5.20 (s) isomers E+Z: OH; 1.01 (d) and 1.08 (d) : $CH_3$—CH; 1.08 (s) and 1.10 (s): 18-Me; 1.45: 19-Me; 2.11 (s) - 2.12 (s): OAc; 3.15 and 3.19: $H_{11}$; 4.49 (d) and 4.67 (d) : C—$CH_2$O; 6.16: $H_4$; 6.20 (dd): $H_2$; 6.61 (d), 6.63 (d): $H_1$.

Analysis of the metals:

Mg-0,1 to 0,2% of the theoretical stoichiometric quantity necessary for the enolate formation.

Alkaline 1 to 2% of the theroical stoichiometric quantity necessary for the enolate formation.

EXAMPLE 2

9β, 11β-epoxy-16α-methyl-Δ1,4-pregna-diene-17α-ol-3,20-dione

Using the procedure of Example 1, 0.02 g of monohydric cupric acetate and 0.649 g of 9β, 11β-epoxy-Δ1,4,16(17)-pregnatriene-3,20-dione in 10 ml of tetrahydrofuran, then 0.8 ml of methyl-magnesium bromide ( 3M in ether) , 8 ml of 13.6% solution of monopotassium phosphate and 1.5 ml of dimethyl sulfide were reacted. Stirring and bubbling through of air were maintained for 16 hours in total and after extraction with ethyl acetate, the crude product was purified by chromatography on silica eluting with methylene chloride - ether mixture (75-25) to obtain 0.326 g of the expected crystallized product.

IR Spectrum ($CHCl_3$)

Absorption at 3610 $cm^{-1}$ (OH), 1706-1688 $cm^{-1}$ (C=O), 1663-1625-1607 $cm^{-1}$ (Δ1,4 3-one).

NMR Spectrum ($CDCl_3$, 300 MHz, ppm)

0.88: 16-$CH_3$; 1.01 (s): 18-$CH_3$; 1.44 (s): 19-$CH_3$; 2.24 (s): —CO—$CH_3$; 3.05 (s) —O—H; 3.21 (s) : $H_{11}$; 6.15: $H_4$; 6.18 (dd): $H_2$; 6.6 (d) : $H_1$.

EXAMPLE 3

16α-methyl-21-acetyloxy-Δ1,4,9(11)-pregnatriene 17α-ol-3,20-dione

Using the procedure of Example 1, 0.02 g of monohydric cupric acetate, 0.733 g of 21-acetyloxy-Δ1,4,9(11), 16 (17)-pregnatetraene-3,20-dione in 10 ml of tetrahydrofuran, then 0.77 ml of methyl-magnesium bromide (3M in ether), 7 ml of 13.6% solution of monopotassium phosphate and 2.25 ml of dimethylsulfide were reacted. The reaction mixture was stirred and bubbling through of air for 18 hours in total. Then, extraction took place with ethyl acetate and the product was purified by chromatography on silica eluting with methylene chloride - ether mixture (7-3) to obtain 0.16 g of the expected crystallized product.

IR spectrum ($CHCl_3$)

Absorption at 3610 $cm^{-1}$ (OH), 1747-1728 $cm^{-1}$ (C=O), 1663-1623-1606 $cm^{-1}$ (Δ1,4 3-one) .

NMR Spectrum ($CDCl_3$, 300 MHz, ppm)

0.75: 13-$CH_3$; 0.94: 16-$CH_3$; 1.40: 10-$CH_3$; 2.17: $CH_3$ of OAC; 4.82 and 4.99: 2H in position 21; 5.54: H in position 11; 6.05: H in position 4; 6.28: H in position 2; 7.19: H in position 1.

EXAMPLE 4

9α-fluoro-16α-methyl-21-acetyloxy-Δ1,4-pregnadiene-11β-17α-diol-3,20-dione

Using the procedure of Example 1, 0.02 g of monohydric cupric acetate and 0.805 g of 9α-fluoro-21-acetyloxy-Δ1, 4,16 (17)-pregnatriene-11β-ol-3,20-dione in 10 ml of tetrahydrofuran, then 1.5 ml of methylmagnesium bromide (3M in ether), 8 ml of 13.6% solution of monopotassium phosphate and 1.6 ml of dimethylsulfide were reacted. The reaction medium was stirred with bubbling through of air for 17 hours in total and then extraction took place with ethyl acetate. The product was purified by chromatography on silica eluting with methylene chloride - ethyl acetate mixture (7-3) to obtain 0.276 g of the expected crystallized product.

IR Spectrum ($CHCl_3$)

Absorptions at 3450-3360 $cm^{-1}$ (OH), 1740 $cm^{-1}$ (C=O/acetate), 1720 $cm^{-1}$ (non conjugated. C=O), 1660 $cm^{-1}$ (conjugated C=O).

NMR Spectrum ($CDCl_3$, 300 MHz, ppm)

0.93 (d): 16-$CH_3$; 1.07: 13-$CH_3$; 1.57: 10-$CH_3$; 2.17:$CH_3$ of OAC; 3.39: 17α OH and 11β-OH; 4.38: 11α-H; 4.92: 2H in position 21; 6.11: H in position 4; 6.33: H in position 2; 7.25: H in position 1.

EXAMPLE 5

9α-fluoro 11β,21-diacetyloxy-16α-methyl-Δ1,4-pregnadiene-17α-ol-3,20-dione

Using the procedure of Example 1, 0.02 g of monohydric cupric acetate and 0.889 g of 9α-fluoro 11β,21-diacetyloxy- Δ1,4,16(17) pregnatriene-3,20-dione in 10 ml of tetrahydrofuran and then 0.78 ml of methylmagnesium bromide (3M in ether), 8 ml of 13.6% solution of monopotassium phosphate and 1.6 ml of dimethylsulfide were reacted. The reaction mixture was stirred with bubbling through of air for 18 hours and then extraction took place with ethyl acetate. The product was purified by chromatography on silica eluting with methylene chloride - ethyl ether mixture (75-25) to obtain 0.634 g of the expected crystallized product.

IR Spectrum (CHCl$_3$)

Absorptions at 3615 cm$^{-1}$ (OH), 1746 cm$^{-1}$ (—OAC), 1730 cm$^{-1}$ (non conjugated C=O), 1668-1631 and 1610 cm$^{-1}$: Δ1,4 3-one.

NMR Spectrum (CDCl$_3$, 300 MHz, ppm)

0.93 (d): CH$_3$ in position 16 and 0.93 (s): CH$_3$ in position 13; 1.58: CH$_3$ in position 10; 2.13-2.15: CH$_3$ of Ac; 2.74: 17α-OH; 4.71-4.99: 2H in position 21; 5.42: H in position 11α; 6.11: H in position 4; 6.33: H in position 2; 6.82: H in position 1.

EXAMPLE 6

9β, 11β-epoxy-16α-methyl-21-acetyloxy-Δ1,4-pregnadiene-17α-ol-3,20-dione

Using the procedure of Example 1, 0.766 g of the 9,11-epoxy derivative and 0.02 g of monohydric cupric acetate in 10 ml of tetrahydrofuran, 0.8 ml of a 3M solution of methyl magnesium bromide in ether and 8 ml of a phosphate buffer solution (1 mol of H$_3$PO$_4$ for 1.2 mol of soda) were reacted. After 5 minutes of stirring under an inert gas atmosphere at 0° C., the temperature was allowed to rise to +18° C. The stirring with the bubbling through of air is continued for 30 minutes and 1.2 ml of tetrahydrothiophene were added. The reaction mixture was stirred with bubbling through of air for 4 hours and another 0.4 ml of tetrahydrothiophene were added and stirring with bubbling through was continued. After decanting and extracting with ethyl acetate, the organic phase was washed with water, dried and the solvent was evaporated. The crude product was purified by chromatography on silica eluting with methylene chloride - ether mixture (7-3) to obtain 0.6075 g of the expected product which was identical to that obtained in Example 1.

Various modifications of the process and intermediates of the invention may be made without departing from the spirit or scope thereof and it is to be understood that the invention is intended to be limited only as defined in the appended claims.

We claim:

1. A process for the preparation of a compound of the formula

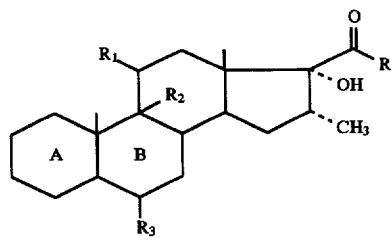

wherein the A and B rings represent a group

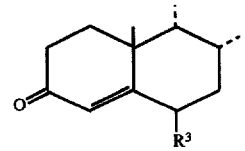

wherein the ketone function in position 3 is optionally protected in the form of a ketal, thioketal, hemithioketal or enol ether, or a group

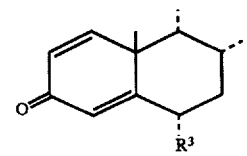

wherein R is methyl or —CH$_2$—OR', R' is hydrogen or an ether or ester remainder; and R$_1$ and R$_2$ form together a second bond or a β-epoxide; or R$_1$ is hydrogen, hydroxy in α- or β-position, said hydroxy being free or protected in the form of an ether or ester, or taken with the free bond forms a keto and R$_2$ is hydrogen; or R$_1$ is hydrogen and R$_2$ is α-hydroxy; or R$_1$ is β-hydroxy, said hydroxy being free or protected in the form of an ether or ester, and R$_2$ is α-fluorine or α-bromine; and R$_3$ is selected from the group consisting of hydrogen, fluorine, α-methyl and β-methyl, comprising reacting a compound of the formula

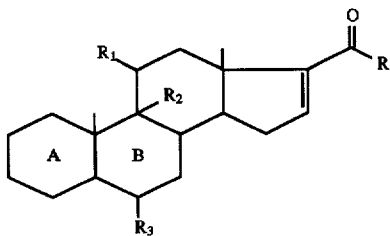

wherein A, B, R, R$_1$, R$_2$ and R$_3$ have the above meaning with a methylation agent selected from the group consisting of a methylated copper derivative, methyl magnesium chloride, methyl magnesium bromide and methyl magnesium iodide in the presence of a copper-based catalyst to form a methylated intermediate, then hydrolyzing the methylated intermediate with a hydrolysis agent to obtain the corresponding enol and oxidizing the enol with molecular oxygen in the presence of a reducing and complexing agent for copper to obtain the compound of Formula I.

2. The process of claim 1 wherein the hydrolysis agent is selected from the group consisting of a) monoalkali metal phosphate, b) a buffer of weakly acidic pH, c) an aqueous solution of ammonium chloride and d) a weak acid.

3. The process of claim 1, wherein in the compound of formula II, the A and B rings are

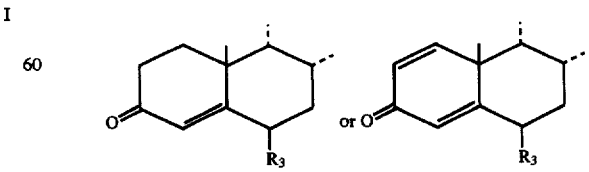

wherein R$_3$ is defined as in claim 1 and the ketone in position 3 is free.

4. The process of claim 1, wherein in the compound of formula II, $R_1$ and $R_2$ form together a second bond, or $R_1$ and $R_2$ form together a β-epoxide, or $R_1$ is β-hydroxy, free or protected in the form of an ether or ester and $R_2$ is β-fluorine, and $R_3$ is hydrogen, fluorine α-methyl or β-methyl.

5. The process of claim 1, wherein in the compound of formula II, $R_3$ is hydrogen.

6. The process of claim 1, wherein the methylation agent is methyl magnesium chloride, bromide or iodide used in the presence of cupric acetate or propionate.

7. The process of claim 1, wherein the enol oxidation is carried out with oxygen or air.

8. The process of claim 1, wherein the reducing and complexing agent of copper is selected from the group consisting of dialkylsulfide, tetrahydrothiophene, trialkylphosphite, triphenylphosphite and triphenylphosphine.

9. The process of claim 1, wherein the reducing and complexing agent of copper is dimethylsulfide or tetrahydrothiophene.

* * * * *